(12) United States Patent
Gribble et al.

(10) Patent No.: US 8,765,781 B2
(45) Date of Patent: *Jul. 1, 2014

(54) BIS-CARBAZOLE DNA INTERCALATING AGENTS FOR ANTITUMOR THERAPY

(75) Inventors: Gordon W. Gribble, Lebanon, NH (US); Dmity A. Androsov, St. Petersburg (RU)

(73) Assignee: Trustees of Dartmouth College, Hanover, NH (US)

( * ) Notice: Subject to any disclaimer, the term of this patent is extended or adjusted under 35 U.S.C. 154(b) by 176 days.

This patent is subject to a terminal disclaimer.

(21) Appl. No.: 13/002,772

(22) PCT Filed: Jul. 2, 2009

(86) PCT No.: PCT/US2009/049560
§ 371 (c)(1),
(2), (4) Date: Jan. 20, 2011

(87) PCT Pub. No.: WO2010/005870
PCT Pub. Date: Jan. 14, 2010

(65) Prior Publication Data
US 2011/0118296 A1    May 19, 2011

Related U.S. Application Data

(60) Provisional application No. 61/078,859, filed on Jul. 8, 2008.

(51) Int. Cl.
    A61K 31/473    (2006.01)
    A61K 31/4709   (2006.01)
    C07D 401/12    (2006.01)

(52) U.S. Cl.
    USPC ............ 514/297; 514/313; 546/105; 546/160

(58) Field of Classification Search
    None
    See application file for complete search history.

(56) References Cited

U.S. PATENT DOCUMENTS

| 2,503,889 | A   |   | 4/1950  | Silven et al. ............ 451/25 |
| 6,187,787 | B1  | * | 2/2001  | Gribble et al. ............ 514/297 |
| 7,135,494 | B2  |   | 11/2006 | Munro et al. ............ 514/411 |
| 7,919,500 | B2  | * | 4/2011  | Gribble et al. ............ 514/285 |

FOREIGN PATENT DOCUMENTS

JP            08044144         *  2/1996

OTHER PUBLICATIONS

STN. Reg. No. 904245-43-8. Entry date of Aug. 24, 2006.*
Williams et al. Foye's Principles of Medicinal Chemistry, 5$^{th}$ Edition, pp. 50 and 59-61, 2002.*
Awada et al. "Clinical Phase I and Pharmacokinetic Study of S 16020, a New Olivacine Derivative: Report on Three Infusion Schedules" Annals of Oncology 2002 13(12):1925-1934.
Gourdie et al. "Synthesis and Evaluation of DNA-Targeted Spatially Separated Bis(aniline mustards) as Potential Alkylating Agents with Enhanced DNA Cross-Linking Capability" Journal of Medicinal Chemistry 1991 34(1):240-248.
Jaycox et al. "Potential DNA bis-Intercalating Agents: Synthesis and Antitumor Activity of Novel, Conformationally Restricted bis(9-Aminoacridines)" Journal of Heterocyclic Chemistry 1987 24(5):1405-1408.
Mayer, A.M.S. and Gustafson, K.R. "Marine Pharmacology in 2001-2: Antitumour and Cytotoxic Compounds" European Journal of Cancer 2004 40(18):2676-2704.
Urban et al. "Coproverdine, a Novel, Cytotoxic Marine Alkaloid from a New Zealand Ascidian" Journal of Natural Products 2002 65(9):1371-1373.
Xu et al. "A High-content Chemical Screen Identifies Ellipticine as a Modulator of p53 Nuclear Localization" Apoptosis 2008 13(3):413-422.
Zhang, A. and Guogiang, L. "The First Synthesis of Clausenamine-A and Cytotoxic Activities of Three Biscarbazole Analogues Against Cancer Cells" Bioorganic & Medicinal Chemistry Letters 2000 10:1021-1023.

* cited by examiner

*Primary Examiner* — Anna Pagonakis
(74) *Attorney, Agent, or Firm* — Licata & Tyrrell P.C.

(57) ABSTRACT

The present invention is a DNA intercalating agent represented by the structure Y—Z—Y, wherein Y is an anti ¬ tumor bis-carbazole and Z is a linear arrangement of multiple aromatic rings, containing at least two aromatic rings, or at least two alicyclic rings, said rings being linked in a 1,4 or 1,3 manner. Methods of inhibiting cancer cells and treating subjects having cancer with these agents are also provided.

2 Claims, No Drawings

BIS-CARBAZOLE DNA INTERCALATING AGENTS FOR ANTITUMOR THERAPY

INTRODUCTION

This application claims benefit of priority to U.S. Provisional Patent Application Ser. No. 61/078,859, filed Jul. 8, 2008, the contents of which are incorporated herein by reference in their entireties.

BACKGROUND OF THE INVENTION

Intercalation is one of several modes by which drugs interact with DNA wherein a planar portion of the drug is inserted in between adjacent stacked base pairs of a double stranded DNA. The intercalation process results in helix extension and unwinding of the DNA. Included within these drugs are antitumor agents, actinomycin D, adriamycin and daunomycin, as well as several drugs for treatment of parasitic disease including ethidium bromide, quinacrine, chloroquine and miracil D. U.S. Pat. No. 2,441,665 discloses a class of alkylene diamine derivatives which are valuable as antimalarial agents. U.S. Pat. No. 2,113,357 discloses basically substituted amino-acridine derivatives useful in treating blood parasites.

DNA intercalating ligands have been proposed for use in targeting alkylating agents to DNA by attachment of the intercalating ligand to the alkylating agent (Gourdie, et al. (1991) *J. Med. Chem.* 34:240-248). Since the biological properties of these DNA intercalating drugs are believed to result from their binding, efforts have focused on designing molecules that have a high affinity for DNA. Planar polycyclic aromatic molecules show a strong propensity to bind to DNA by intercalation (Jaycox, et al. (1987) *J. Heterocyclic Chem.* 24:1405-1408). To identify molecules with a greater affinity and selectivity for DNA, bifunctional intercalating agents in which two intercalating ligands are bridged by a central linking chain have been developed, wherein enhanced binding has been observed with molecules of this type (Canellakis, et al. (1976) *Biochim. Biophys. Acta* 418:277; Becker & Dervan (1979) *J. Am. Chem. Soc.* 101:3664; Wakelin, et al. (1986) *Med. Res. Rev.* 6:275). However, the chemical and physical nature of the linking chain has been found to play a role in the binding process.

For example, bis-intercalators bridged by flexible chains generally exhibit reduced affinities for DNA, in part because of self-stacking interactions which compete with the binding process (Barbet, et al. (1976) *Biochemistry* 15:2642; Capelle, et al. (1979) Biochemistry 18:3354). Further, bis-intercalation can introduce undesirable entropic effects when a flexible linker is forced into an extended chain conformation (Jaycox, et al. (1987) *J. Heterocyclic Chem.* 24:1405-1408). In addition, it is a concern that flexible bis-intercalators can creep in a stepwise fashion along the DNA macromolecule, thereby lowering ligand residence lifetimes at any one site (Denny, et al. (1985) *J. Med. Chem.* 28:1568). Such a process could have significant effects on efficacy of these intercalators as anticancer agents as residence lifetimes have been correlated with in vivo antitumor activity for a large number of DNA intercalators (Feigon, et al. (1984) *J. Med. Chem.* 27:450). Rigid tethers have been suggested as an (Jaycox, et al. (1987) *J. Heterocyclic Chem.* 24:1405-1408; U.S. Pat. No. 6,187,787).

SUMMARY OF THE INVENTION

The present invention relates to compounds of the structure Y—Z—Y, wherein Y is an anti-tumor bis-carbazole and Z is a linear arrangement of at least two aromatic rings or two acyclic rings arranged in a 1, 4 or 1,3 configuration.

Methods of inhibiting cancer cell growth and treating cancer in a subject using a compound of the invention are also provided.

DETAILED DESCRIPTION OF THE INVENTION

The present invention relates to bis-carbazoles as DNA intercalating agents for use in the treatment of cancer. The bis-intercalators of the invention contain semi-rigid tethers that link two bis-carbazoles molecules, e.g., two pyridocarbazole molecules.

Compounds of the invention are represented by the structure Y—Z—Y, wherein Y is an anti-tumor bis-carbazole and Z is a linear arrangement of at least two aromatic rings or two acyclic rings arranged in a 1, 4 or 1,3 configuration.

"Anti-tumor bis-carbazoles" are bis-carbazole compounds that exhibit anti-tumor activity in in vitro and/or in vivo assays. Anti-tumor bis-carbazoles are well-known and described in the art. For example, the plant alkaloid ellipticine is well-known for its cytostatic activity (Dalton, et al. (1967) *Aust. J. Chem.* 20:2715; Svoboda, et al. (1968) *J. Pharm. Sci.* 57:1720). Similarly, U.S. Pat. No. 7,135,494 (incorporated herein by reference) discloses a series of carbazole molecules exhibiting anti-tumor activity. Moreover, it has been shown that olivacine and 9-hydroxyellipticine are potent anti-tumoral agents (Sethi (1981) *Biochem. Pharmacol.* 30:2026), as is the olivacine derivative S 16020-2 (Guilbaud, et al. (1996) *Cancer Chemother. Pharmacol.* 38:513-521). See also U.S. Pat. No. 4,851,417 and U.S. Patent Application No. 2007/0054905. The cytotoxicity of ellipticines, elliptinium and 9-hydroxy-derivatives such as 2-methyl-9-hydroxyellipticinium (NSC 264-137) has also been demonstrated (Paoletti, et al. (1980) *Recent Res. Cancer Res.* 74:107-112). In particular embodiments, Y is selected from the group of anti-tumor bis-carbazoles including, but not limited to 1,4-dimethyl-carbazole (PubChem Compound ID 96998) and pyridocarbazoles such as Ellipticine (PubChem Compound ID 5288156), 9-Methoxyellipticine (PubChem Compound ID 72512), 9-Hydroxyellipticin (PubChem Compound ID 91643), Celiptium (Elliptinium, PubChem Compound ID 42722), Bis-Elliptinium Bromide, 6-Methyl-Ellipticine (PubChem Compound ID 97109), Ellipticine N-oxide (PubChem Compound ID 315033), Ellipticine Derivative NSC359449 (PubChem Compound ID 5458841), 6-(5-Hexen-1-yl)ellipticine (PubChem Compound ID 294454), 9-Bromoellipticine (PubChem Compound ID 97080), Olivacine (PubChem Compound ID 5281407), Thioolivacine (PubChem Compound ID 278065), S16020-2 (NSC-D-659687, (PubChem Compound ID 177329), 2-Methyl-9-hydroxyellipticinium (PubChem Compound ID 3034753), NSC311153 (PubChem Compound ID 3086132), and NSC311152 (PubChem Compound ID 3086131).

As indicated, Z is a linear arrangement of at least two aromatic rings or two acyclic rings arranged in a 1,4 or 1,3 configuration. In particular embodiments, Z is selected from a group of:

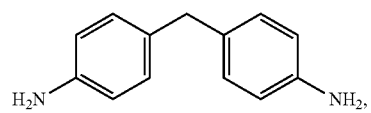

-continued

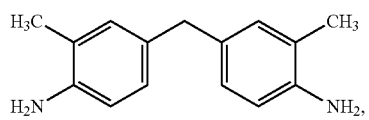
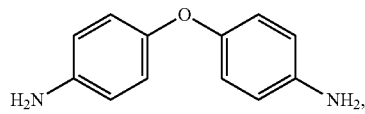
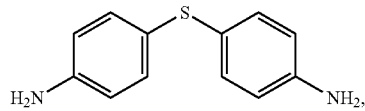
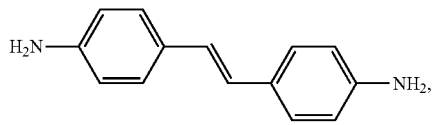
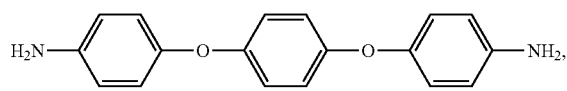
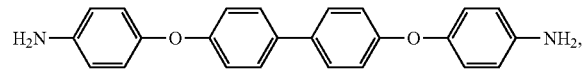
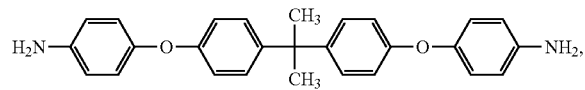
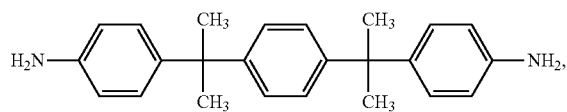
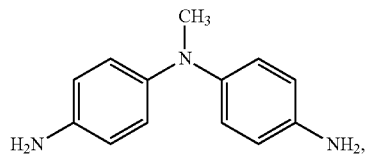
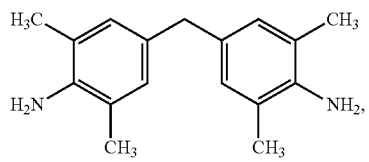
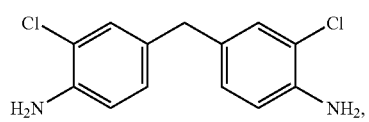
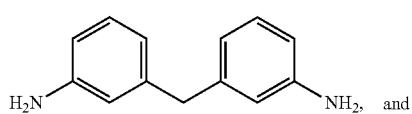, and -continued

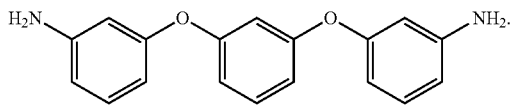

In particular embodiments, Z is attached via covalent bonds to NH or methyl groups of bis-carbazole compounds, e.g., using the methods disclosed herein. In addition, it is contemplated that Z can also be attached to any benzene ring of the bis-carbazole compounds of the invention.

U.S. Pat. Nos. 2,503,889 and 6,187,787 respectively disclose halogenated diacridine compounds and aminoacridine compounds with similar linking chains.

The compounds of the present invention are for use in binding to DNA in a tighter fashion than DNA intercalation agents currently in clinical use for the treatment of cancer. In addition, the compounds of the present invention are contemplated as being more effective inhibitors of cancer cells than the anti-tumor carbazoles disclosed in the prior art. Accordingly, compounds of the present invention will be useful in treating subjects suffering from cancer, such as leukemia, breast cancer, kidney cancer, lung cancer and the like. Indeed, it is contemplated that any cancer conventionally treated with an anti-tumor carbazole will likewise be treated with a compound of the present invention.

The compounds disclosed herein can be synthesized according the procedures disclosed herein or any other suitable means of synthesis. Similarly, DNA binding and efficacy in the treatment of cancer can be demonstrated using conventional methods. For example, thermal denaturation studies can be performed on calf thymus DNA (see, e.g., Fiel, et al. (1979) *Nucleic Acids Res.* 6(9):3093-118; Nakaike, et al. (1992) *Jpn. J. Cancer Res.* 83(4):402-9; Fairley, et al. (1993) *J. Med. Chem.* 36(12):1746-53). In addition, the compounds can be analyzed for their ability to exhibit cytotoxicity in suitable cell line or animal models of cancer. For example, the murine leukemia cell line, L1210, is used in in vitro assays (Jaycox, et al. (1987) *J. Heterocyclic. Chem.* 24:1405-1408), as well as in in vivo assays, wherein CD2F1 mice receive L1210 leukemia cells by intraperitoneal injection (Edanami, et al. (1984) *Cancer Chemother Pharmacol.* 13(1):22-6; Douzono, et al. (1995) *Jpn. J. Cancer Res.* 86(3):315-21). Similarly, the human mammary carcinoma MX-1 xenograft model is routinely used in the preclinical analysis of anti-tumor compounds in the treatment of breast cancer (Zhao, et al. (2008) *Bioconjug Chem.* 19(4):849-59; Wada, et al. (2007) *Anticancer Res.* 27:1431-5; Donawho, et al. (2007) *Clin Cancer Res.* 13:2728-37). In this model, NU/NU Swiss (nude) mice receive an intrarenal inoculation of MX-1 cells prior to or after treatment with the test compound. The human lung LX-1 xenograft model, wherein nude mice receive an intrarenal inoculation of LX-1 tumor cells, is also routinely used in the preclinical analysis of anti-tumor compounds (Masuda, et al. (2006) *J. Antibiot.* (Tokyo) 59(4):209-14). Similar models exist for the analysis of anti-tumor activity in prostate cancer (e.g., the TRAMP model, wherein transgenic mice develop spontaneous prostate cancer), skin cancer (e.g., the Mouse B16 Melanoma model), ovarian cancer (mouse ovarian carcinoma xenograft model; Davis, et al. (1993) *Cancer Research* 53:2087-2091) and kidney cancer (e.g., the murine renal cell carcinoma model (RENCA model)). Indeed, any suitable rodent or primate model can be used in the analysis of anti-tumor activity of the instant compounds. In each of these models, survival and/or tumor size is measured and the results are expressed as the measurement made in the treated group divided by the measurement made in the vehicle treated control group. Results of this analysis are expected to demonstrate that tumor size is decreased and or survival is increased in animals receiving treatment with a compound of the present invention.

Accordingly, the present invention also relates to methods of treating cancer, wherein an effective amount of a compound of the present invention is administered to the subject in need of treatment so that growth of the cancer cells is inhibited or decreased and the signs or symptoms of the cancer are ameliorated, decreased or reversed. In a particular embodiment, the compound is administered in a pharmaceutically acceptable carrier. Suitable pharmaceutically acceptable carriers are well-known in the art and are described for example in Remington: The Science and Practice of Pharmacy, Alfonso R. Gennaro, editor, 20th ed. Lippincott Williams & Wilkins: Philadelphia, Pa., 2000, a standard reference text in this field. Pharmaceutical carriers can be selected in accordance with the intended route of administration and the standard pharmaceutical practice. In a particular embodiment, an effective amount of compound of the present invention is administered to a subject intravenously or intratumorally and can be linked to a carrier which selectively targets tumor cells (e.g., an antibody). By "effective amount" it is meant a concentration or dose of a compound of the present invention which will inhibit cancer cell growth. Such dosages can be calculated routinely by those of skill in the art in accordance with in vitro and/or in vivo data from model systems and dosages used for other DNA intercalating agents in clinical use.

The invention is described in greater detail by the following non-limiting examples.

Example 1

Synthesis of Bis-Imines and Bis-Amines

General Procedure for the Synthesis of Bis-Imines (3).

1,4-Dimethyl-9H-carbazole-3-carbaldehyde 1 (2 mmol), aryldiamine 2 (1 mmol), PTSA (catalytic amount—1 crystal) and toluene or benzene (100 ml) were charged into 250 ml round bottom flask. The mixture was refluxed with Dean-Stark distilling trap for 12 hours. After completion of the reaction, solvent was removed under reduced pressure, and solid residue was crystallized from $CH_2Cl_2$-MeOH to give the corresponding bis-imine 3 (Scheme 1).

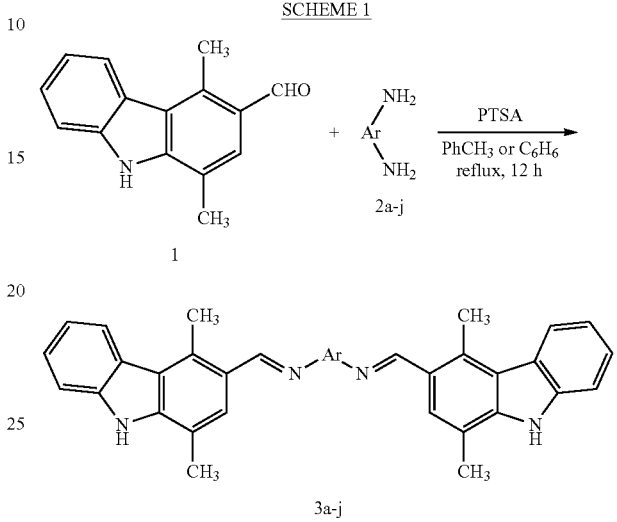

General Procedure for the Synthesis of Bis-Amines (4).

MeOH (100 ml) was added to the solution of bis-imine 3 (1 mmol) in DMF (10 ml) and the mixture was stirred and heated to reflux. $NaBH_4$ (5 mmol) was added portion wise (during a 5-minute period) and the mixture was refluxed for the additional 10 minutes. After cooling, MeOH was removed under reduced pressure and the residue was poured into water to give the precipitate of crude bis-amine 4 (Scheme 2). Bis-amine 4 was collected by suction and washed with water thoroughly. Recrystallization from $CH_2Cl_2$-MeOH afforded pure 4 as crystalline solid.

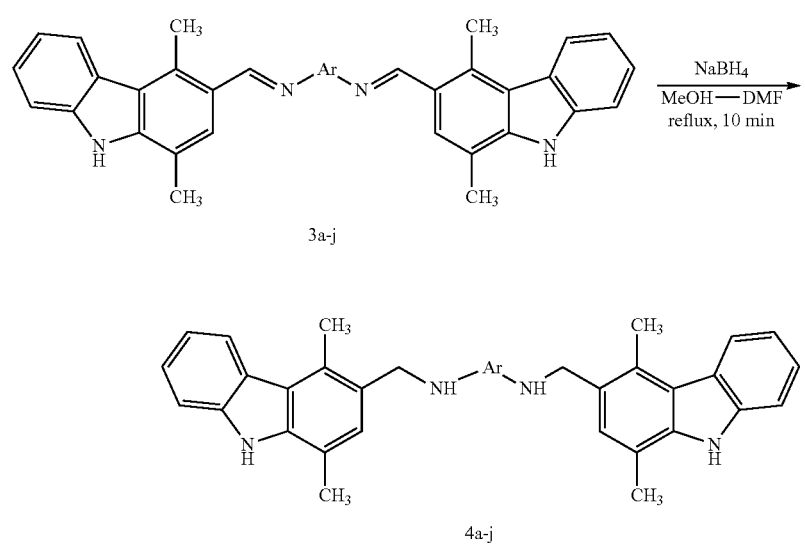

Yields of bis-carbazoles (3) and (4) are listed in Table 1.
TABLE 1
| Ar | Yield (%) | |
| --- | --- | --- |
| | Comp. 3 | Comp. 4 |
| 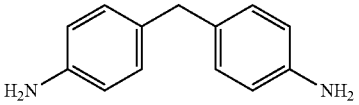<br>2a | 53 | 80 |
| 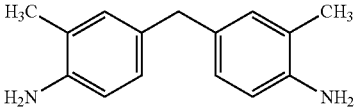<br>2b | 55 | 97 |
| 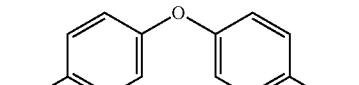<br>2c | 75 | 85 |
| 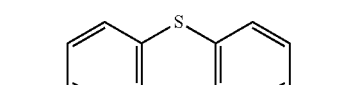<br>2d | 47 | 67 |
| 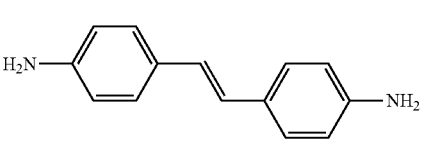<br>2e | 77 | 64 |
| 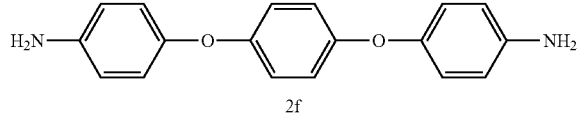<br>2f | 41 | 75 |
| 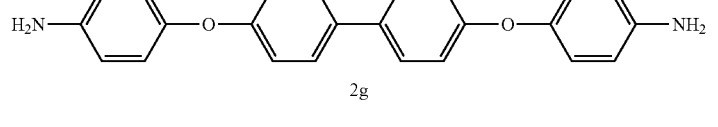<br>2g | 38 | 98 |
| 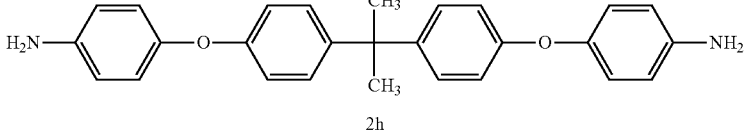<br>2h | 12 | 90 |
| 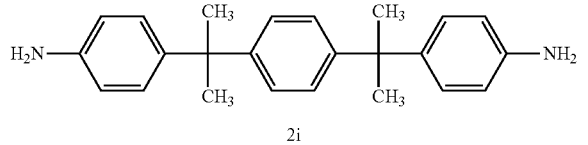<br>2i | 77 | 83 |

TABLE 1-continued

| | Yield (%) | |
|---|---|---|
| Ar | Comp. 3 | Comp. 4 |
| 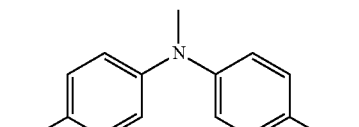 2j | — | 50 |

Example 2

Synthesis of Bis-Acetylamine (5)

Bis-amine 4a (1 mmol) and Et$_3$N (2.5 mmol) were dissolved in CHCl$_3$ (50 ml) and the solution of acetyl chloride (2.2 mmol) in CHCl$_3$ (10 ml) was added dropwise at vigorous stirring. Subsequently, the mixture was stirred and refluxed for an additional 5 minutes. Addition of MeOH (50 ml) and displacement of CHCl$_3$ caused crystallization of the solid (Scheme 3). Bis-acetylamine 5 was filtered by suction, washed with MeOH, and recrystallized from CHCl$_3$-MeOH to give 5 (66% yield) as a white solid.

SCHEME 4

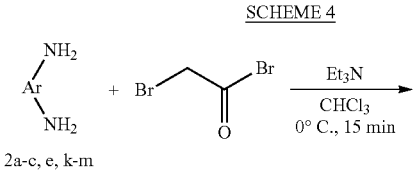

SCHEME 3

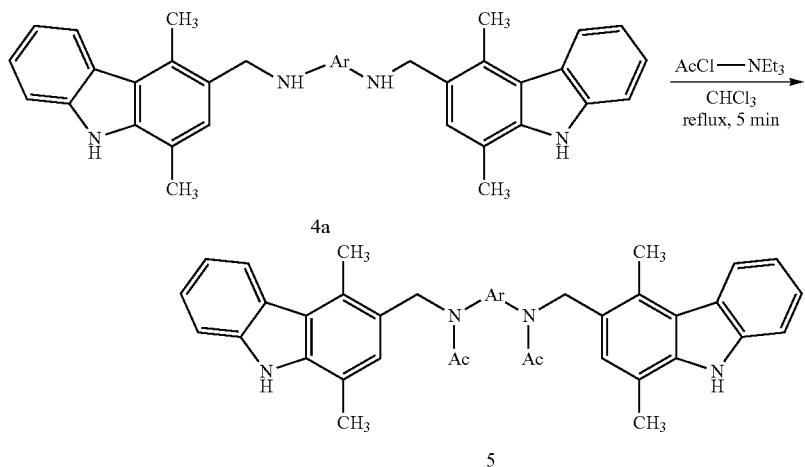

Example 3

Synthesis of Bis-Elliptinium Bromides and Precursors

General Procedure for the Synthesis of Bis-Bromoacetyl Bromides (6).

A solution of bromoacetyl bromide (2.2 mmol) in CHCl$_3$ (10 ml) was added dropwise to the solution of bis-amine 2 (1 mmol) and Et$_3$N (2.5 mmol) in CHCl$_3$ (30 ml) at 0° C. The resulting mixture was stirred for an additional 15 minutes at 0° C. Addition of MeOH (30 ml) and displacement of CHCl$_3$ at a low temperature (10-20° C., rotary evaporator) caused precipitation of 6 (Scheme 4). Bis-bromoacetyl bromide 6 was filtered by suction washed with small amount of MeOH, dried at room temperature, and used further without additional purification.

-continued

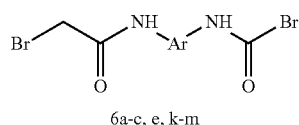

6a-c, e, k-m

General Procedure for the Synthesis of Bis-Elliptinium Bromides (8).

A Solution of bis-bromoacetyl bromide 6 (1 mmol) and ellipticine (2 mmol) in DMSO (10 ml) was stirred and heated at 100° C. for 12 hours. After cooling, i-PrOH (30 ml) was added to precipitate solid 8 (Scheme 5). Bis-elliptinium bromide 8 was filtered by suction, washed with i-PrOH, and dried at 70° C.

SCHEME 5

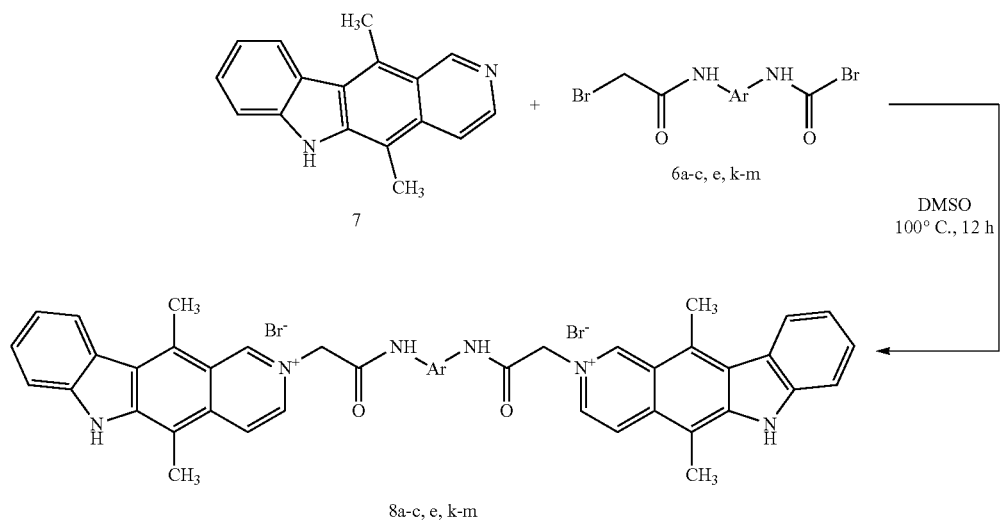

Yields of bis-elliptinium bromides (8) and the precursors (6) are listed in Table 2.

TABLE 2

| Ar | Yield (%) Comp. 6 | Yield (%) Comp. 8 |
|---|---|---|
| 2a | 47 | 53 |
| 2b | 53 | 60 |
| 2c | 52 | 34 |
| 2e | 71 | 69 |
| 2k | 65 | 63 |
| 2l | 70 | 49 |
| 2m | 68 | 70 |

Example 4

Cytotoxicity Evaluation in Leukemia Cells

L1210 murine leukemia cells are maintained as suspension cultures in McCoy's 5A medium supplemented with 10% horse serum, glutamine, penicillin, and streptomycin and grown in a humidified environment of 10% carbon dioxide and 90% air at 37° C. Compounds are dissolved in dimethyl sulfoxide (DMSO) and 40 μg of compound is added to 4 ml of L1210 cells ($10^5$ cells/tube) to attain final drug concentrations of 0.01, 0.1 and 10 μg/ml of culture. After hours of continuous exposure to the drug, the cell concentration is determined by a Coulter counter (Model ZBF, Hialeah, Fla.). Growth inhibition is calculated for each drug concentration using the following formula:

$$\% \text{ Growth Inhibition} = (1-A) \times 100,$$

wherein A=[cell number treated/cell number in DMSO alone].

What is claimed is:
1. A compound consisting of the structure Y—NH—Z—NH—Y, Y=N—Z—N=Y, Y—N(Ac)—Z—N(Ac)—Y, or Y—C(O)—NH—Z—NH—C(O)—Y, wherein
(a) Z is selected from a group of:
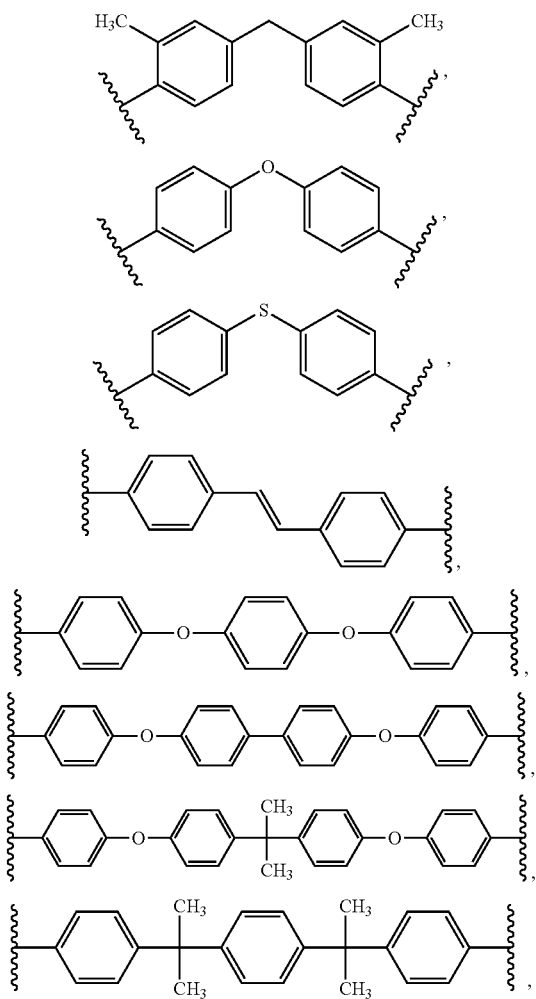
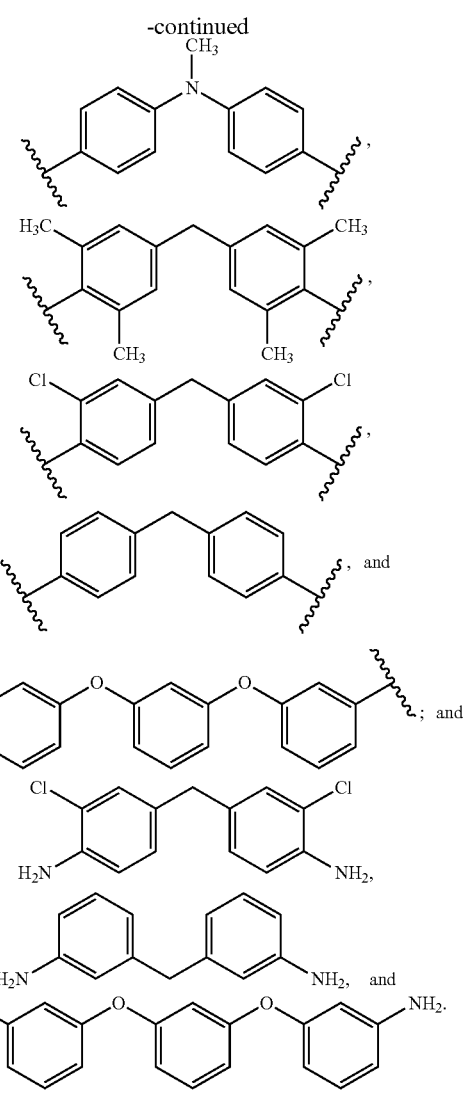
(b) Y is a pyridocarbazole.
2. A pharmaceutical composition comprising a compound of claim 1 in a pharmaceutically acceptable carrier.
* * * * *